(12) United States Patent
Hershberger et al.

(10) Patent No.: US 11,944,686 B2
(45) Date of Patent: Apr. 2, 2024

(54) CANNABINOID CONJUGATE MOLECULES

(71) Applicant: Akos Biosciences, Inc, Naples, FL (US)

(72) Inventors: Paul M. Hershberger, Indialantic, FL (US); Yinghui Liu, Ann Arbor, MI (US); Kirk William Hering, Salem, OR (US); James Bernard Kramer, Sylvania, OH (US); Ramanathan S. Lalgudi, Westerville, OH (US)

(73) Assignee: AKOS BIOSCIENCES, INC., Naples, FL (US)

( * ) Notice: Subject to any disclaimer, the term of this patent is extended or adjusted under 35 U.S.C. 154(b) by 0 days.

(21) Appl. No.: 18/137,766

(22) Filed: Apr. 21, 2023

(65) Prior Publication Data

US 2023/0256104 A1     Aug. 17, 2023

Related U.S. Application Data

(63) Continuation of application No. 17/982,779, filed on Nov. 8, 2022, and a continuation of application No. 17/982,859, filed on Nov. 8, 2022, now Pat. No. 11,660,348.

(60) Provisional application No. 63/321,341, filed on Mar. 18, 2022, provisional application No. 63/321,360, filed on Mar. 18, 2022, provisional application No. 63/321,319, filed on Mar. 18, 2022, provisional application No. 63/312,695, filed on Feb. 22, 2022, provisional application No. 63/305,339, filed on Feb. 1, 2022.

(51) Int. Cl.
    *A61K 47/55*     (2017.01)
    *A61K 47/54*     (2017.01)

(52) U.S. Cl.
    CPC ................... *A61K 47/545* (2017.08)

(58) Field of Classification Search
    CPC ..................................................... A61K 47/55
    See application file for complete search history.

(56) References Cited

U.S. PATENT DOCUMENTS

| | | |
|---|---|---|
| 5,847,128 A | 12/1998 | Martin et al. |
| 7,053,150 B2 | 5/2006 | Kozlowski et al. |
| 8,022,059 B2 | 9/2011 | Yamaguchi et al. |
| 8,293,786 B2 | 10/2012 | Stinchcomb et al. |
| 9,533,942 B2 | 1/2017 | Stinchcomb et al. |
| 2008/0176885 A1 | 7/2008 | Holtman et al. |
| 2009/0143462 A1 | 6/2009 | Stinchcomb et al. |
| 2014/0302121 A1 | 10/2014 | Bevier |
| 2021/0009549 A1 | 1/2021 | Jagtap et al. |
| 2021/0137987 A1 | 5/2021 | Novina et al. |
| 2021/0228699 A1 | 7/2021 | Novina et al. |
| 2022/0273805 A1 | 9/2022 | Hershberger et al. |

FOREIGN PATENT DOCUMENTS

| | | |
|---|---|---|
| CN | 1475482 A | 2/2004 |
| CN | 109942505 A | 6/2019 |
| CN | 107722057 A | 7/2019 |
| WO | 1995020567 A1 | 8/1995 |
| WO | 2004037798 A1 | 5/2004 |
| WO | 2009041559 | 4/2009 |
| WO | 2011082368 A2 | 7/2011 |
| WO | 2014197854 A1 | 12/2014 |
| WO | 2017072196 A1 | 5/2017 |
| WO | 2019222459 A1 | 11/2019 |
| WO | 2020006312 A1 | 1/2020 |
| WO | 2020214220 A2 | 10/2020 |
| WO | 2020263888 A1 | 12/2020 |
| WO | 2020263893 A1 | 12/2020 |
| WO | 2020263975 A1 | 12/2020 |
| WO | 2021034405 A1 | 2/2021 |
| WO | 2021076197 A1 | 4/2021 |
| WO | 2021243467 A1 | 12/2021 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
PUBCHEM-CID: 101614426, Dec. 18, 2015, pp. 1-8.
Howbert et al., Novel Agents Effective against Solid Tumors: The Diarylsulfonylureas. Synthesis, Activities, and Analysis of Quantitative Structure-Activity Relationships, Journal of Medicinal Chemistry, 1990, vol. 33, No. 9.
Jasmeet Kaur, Diclofenac, A Selective COX-2 Inhibitor, Inhibits DMH-Induced Colon Tumorigenesis Through Suppression of MCP-1, MIP-1a and VEGF, Molecular Carcinogenesis, vol. 50, pp. 707-718, Published Jan. 25, 2011 by Wiley Online Library.

* cited by examiner

*Primary Examiner* — Nizal S Chandrakumar
(74) *Attorney, Agent, or Firm* — Lippes Mathias LLP

(57) ABSTRACT

Disclosed are conjugate molecules formed from an active agent which is linked to a cannabinoid moiety through a specified linker having ester and amide end groups. The active agent can be a COX-2 inhibitor moiety, and the cannabinoid moiety can be a cannabidiol moiety. These conjugate molecules are contemplated to potentially be effective in the treatment of medical conditions.

4 Claims, 11 Drawing Sheets meloxicam (3a)

CANNABINOID CONJUGATE MOLECULES

CROSS-REFERENCE TO RELATED APPLICATIONS

This application is a continuation of U.S. patent application Ser. No. 17/982,779, filed on Nov. 8, 2022, now U.S. Pat. No. /insert later/, which claims priority to U.S. Provisional Patent Application Ser. No. 63/321,360, filed on Mar. 18, 2022, and to U.S. Provisional Patent Application Ser. No. 63/321,341, filed on Mar. 18, 2022, and to U.S. Provisional Patent Application Ser. No. 63/321,319, filed on Mar. 18, 2022, and to U.S. Provisional Patent Application Ser. No. 63/312,695, filed on Feb. 22, 2022, and to U.S. Provisional Patent Application Ser. No. 63/305,339, filed on Feb. 1, 2022, each of which is incorporated by reference in its entirety. This application is also a continuation of U.S. patent application Ser. No. 17/982,859, filed on Nov. 8, 2022, now U.S. Pat. No. /insert later/, which claims priority to U.S. Provisional Patent Application Ser. No. 63/321,360, filed on Mar. 18, 2022, and to U.S. Provisional Patent Application Ser. No. 63/321,341, filed on Mar. 18, 2022, and to U.S. Provisional Patent Application Ser. No. 63/321,319, filed on Mar. 18, 2022, and to U.S. Provisional Patent Application Ser. No. 63/312,695, filed on Feb. 22, 2022, and to U.S. Provisional Patent Application Ser. No. 63/305,339, filed on Feb. 1, 2022, each of which is incorporated by reference in its entirety.

BACKGROUND

The present disclosure relates to conjugate molecules containing an active agent and a cannabinoid moiety. It finds particular application in conjunction with medical applications, and will be described with particular reference thereto. However, it is to be appreciated that the present disclosure is also amenable to other like applications.

BRIEF DESCRIPTION

The present disclosure relates generally to conjugate molecules formed from an active agent which is linked to a cannabinoid moiety through a specified linker. In more particular embodiments, the active agent is a COX-2 inhibitor moiety, and the cannabinoid moiety is a cannabidiol moiety. These conjugate molecules are contemplated to potentially be effective in the treatment of medical conditions. Such medical conditions might include inflammatory conditions such as arthritis, or pain management.

These and other non-limiting aspects of the disclosure are more particularly set forth below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1A:
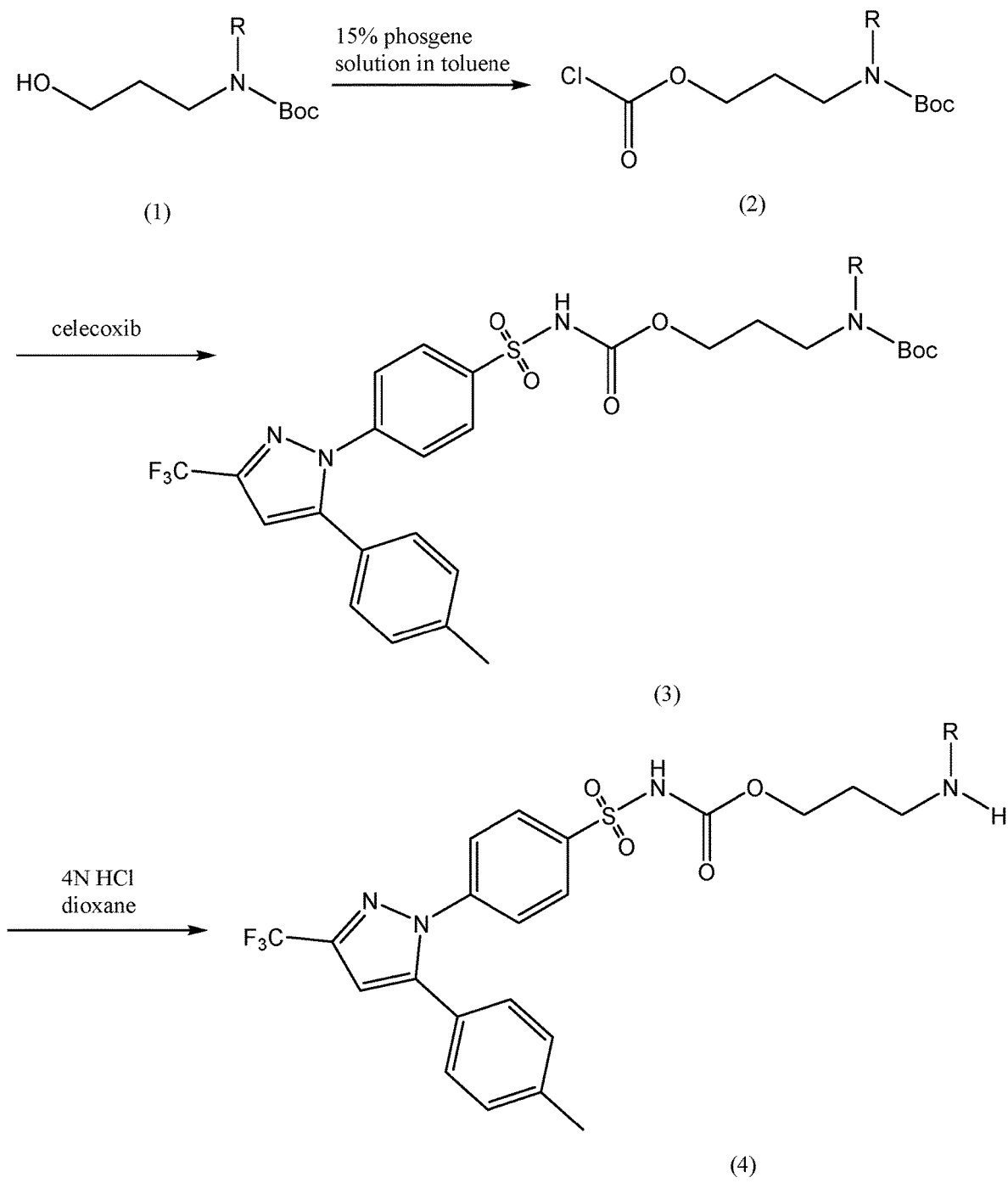
FIG. 1A is the first part of a synthetic route for preparing a conjugate molecule, in some embodiments.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

The phrase "pharmaceutically effective amount" means a sufficient amount of the compound to treat the subject and obtain the desired therapeutic benefit at a reasonable benefit/risk ratio applicable to any medical treatment. It will be understood, however, that the total daily usage of the compositions of the present disclosure will be decided by the attending physician or other care provider within the scope of sound medical judgment. The specific therapeutically effective dose level for any particular patient will depend upon a variety of factors, including the disorder being treated and the severity of the disorder; medical history of the patient, age, body weight, general health, sex and diet of the patient, the time of administration, route of administration, the duration of the treatment, other drugs being taken by the patient, and the like. A single administration may be sufficient to produce a therapeutic effect, but it is contemplated that multiple administrations will be used over a substantial period of time to assure continued response.

The present disclosure relates to conjugate molecules which are contemplated to be useful in the treatment of various medical conditions, such as for pain management, or for inflammatory conditions, or for arthritis. Compositions including these conjugate molecules are also contemplated, as well as methods of making and using these conjugate molecules.

Conjugate Molecule

Very generally, the conjugate molecules are formed from an active agent which is linked to a cannabinoid moiety through a specified linker. It is contemplated that both the active agent and the cannabinoid will have a therapeutic effect when delivered to the desired location. The conjugate molecule can remain intact, or a covalent bond can be broken so that the active agent and the cannabinoid become two separate molecules. Such conjugate molecules are illustrated in Formula (I) below:

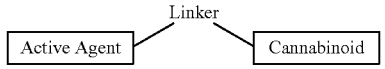

Formula (I)

where the linker covalently bonds the active agent to the cannabinoid moiety.

In particular embodiments, the linker may comprise an alkyl chain with heteroatomic end groups. Examples of such heteroatomic end groups can include an ester group and an amide group.

The active agent may be any agent that can be used to treat a medical condition. Some non-limiting examples of active agents may include celecoxib or diclofenac, which can be used for pain management. More desirably, the active agent has an acidic hydrogen atom attached to a nitrogen atom, for example a primary or secondary amino group. The linker can be reacted to remove the acidic hydrogen atom and form a covalent bond with the nitrogen atom. Even more desirably, the active agent also does not have any hydroxyl groups, so that the reaction of the linker is directed to the nitrogen atom.

In other embodiments, the active agent has a carboxylic acid group. The linker can also be reacted to form a covalent bond with the non-carbonyl oxygen atom. In more desirable embodiments, the active agent also does not contain any primary or secondary amino groups, or does not contain any acidic hydrogen atom attached to a nitrogen atom.

In particular embodiments, the active agent is a COX-2 inhibitor moiety. The COX-2 inhibitor moiety targets cyclooxygenase-2 (COX-2). Non-limiting examples of various COX-2 inhibitor moieties may include celecoxib; cimicoxib; etoricoxib; lumiracoxib; parecoxib; polmacoxib; rofecoxib; valdecoxib; bromfenac; etodolac; ketorolac tromethamine; meloxicam; nabumetone; and oxaprozin. These compounds are illustrated below:

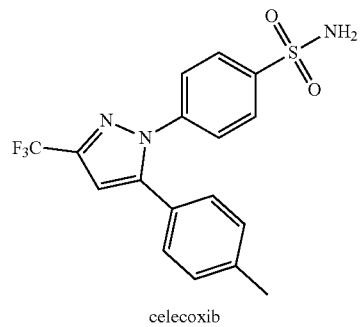

celecoxib

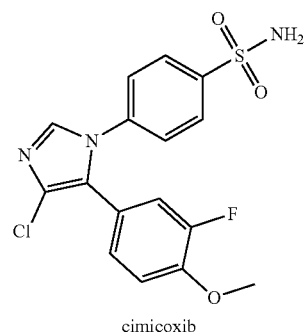

cimicoxib

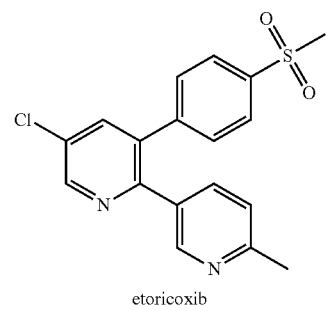

etoricoxib

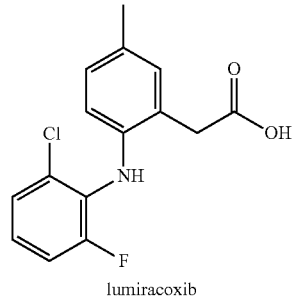

lumiracoxib

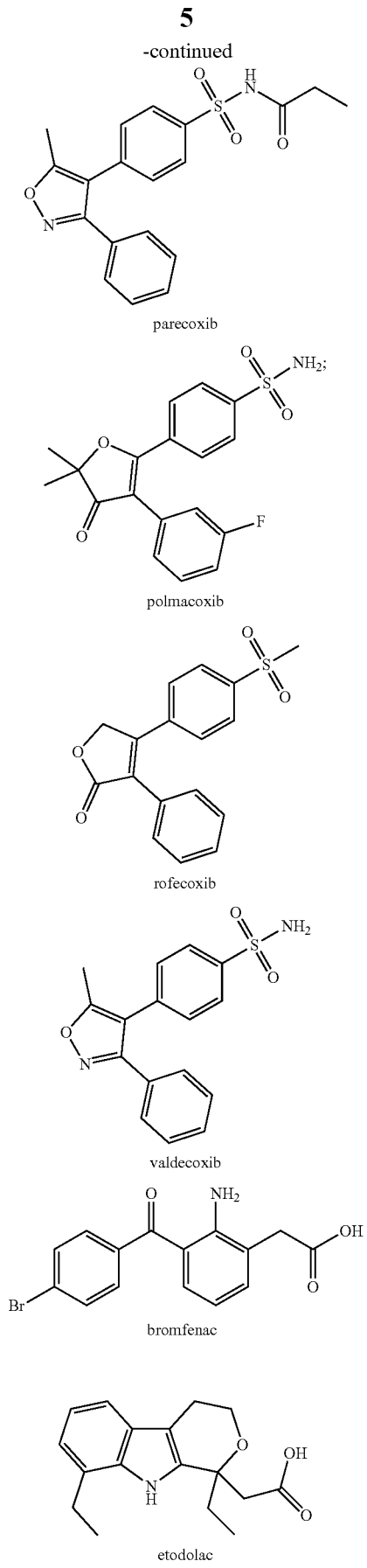

parecoxib polmacoxib rofecoxib valdecoxib bromfenac etodolac

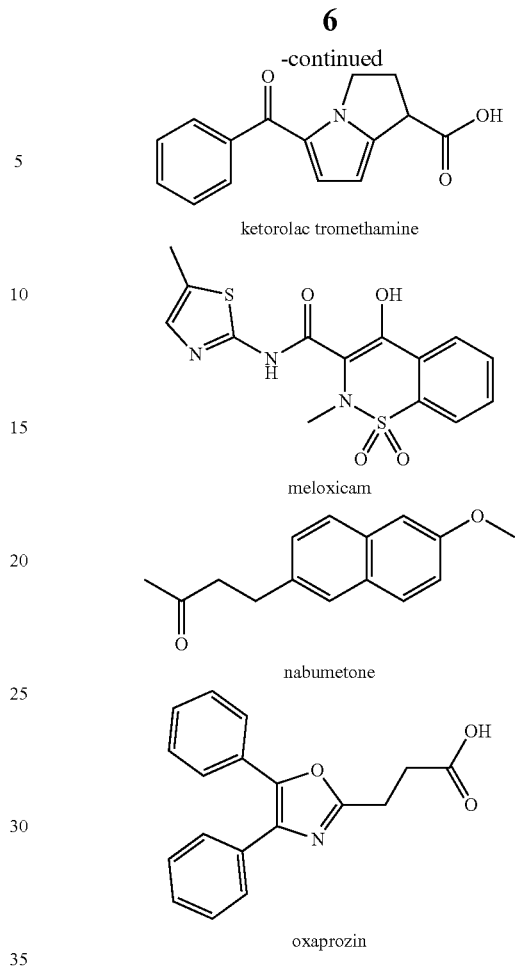

ketorolac tromethamine meloxicam nabumetone oxaprozin

The COX-2 inhibitor moieties may take any form, such as salts, acids, esters, analogs, derivatives, or prodrugs thereof, etc.

The cannabinoid moiety can be any cannabinoid or derivative thereof. For example, the cannabinoid can be a cannabidiol, cannabigerol, cannabichromene, tetrahydrocannabinol, cannabicyclol, cannabielsoin, cannabinol, cannabinodiol, cannabitriol, dehydrocannabifuran, cannabifuran, cannabichromanon, or cannabiripsol.

Examples of cannabidiols include cannabidiolic acid (CBDA), cannabidiol (CBD), cannabidiol monomethylether (CBDM), cannabidiol-C4 (CBD-C4), cannabidivarinic acid (CBDVA), cannabidivarin (CBDV), and cannabidiorcol (CBD-Ci).

Examples of cannabigerols include cannabigerolic acid (CBGA), cannabigerolic acid monomethylether (CBGAM), cannabigerol (CBG), cannabigerol monomethyleither (CBGM), cannabigerovarinic acid (CBGVA), and cannabigerovarin (CBGV).

Examples of cannabichromenes include cannabichromenic acid (CBC), cannabichromene (CBC), cannabichromevarinic acid (CBCVA), and cannabichromevarin (CBCV).

Examples of tetrahydrocannabinols include D-9-tetrahydrocannabinolic acid A (THCA-A), D-9-tetrahydrocannabinolic acid B (THCA-B), D-9-tetrahydrocannabinol (THC), D-9-tetrahydrocannabinolic acid-C4 (THCA-C4), A-9-tetrahydrocannabinol-C4 (THC-C4), D-9-tetrahydrocannabivarinic acid (THCVA), D-9-tetrahydrocannabivarin (THCV), D-9-tetrahydrocannabiorcolic acid (THCA-Ci), D-9-tetrahydrocannabiorcol (THC-Ci), D-7-cis-tetrahydrocannabivarin, D-8-tetrahydrocannabinolic acid (Δ⁸-THCA), and D-8-tetrahydrocannabinol (Δ⁸-THC).

Examples of cannabicyclols include cannabicyclolic acid (CBLA), cannabicyclol (CBL), and cannabicyclovarin (CBLV).

Examples of cannabielsoins include cannabielsoic acid A (CBEA-A), cannabielsoic acid B (CBEA-B), and cannabielsoin (CBE).

Examples of cannabinols and cannabinodiols include cannabinolic acid (CBNA), cannabinol (CBN), cannabinol-C4 (CBN-C4), cannabivarin (CBV), cannabinol-C2 (CBN-C2), cannabiorcol (CBN-Ci), cannabinodiol (CBND), and cannabinodivarin (CBVD).

Examples of cannabitriols include cannabitriol (CBT), 10-ethoxy-9-hydroxy-A-6a-tetrahydrocannabinol, cannabitriolvarin (CBTV), and ethoxy-cannabitriolvarin (CBTYE).

Cannabifurans include dehydrocannabifuran (DCBF) and cannabifuran (CBF).

Examples of other cannabinoids include cannabichromanon (CBCN), 10-oxo-A-6a-tetrahydrocannabinol (OTHC), cannabiripsol (CBR), and trihydroxy-D-9-tetrahydrocannabinol (triOH-THC).

Derivatives of such cannabinoids may be used as the cannabinoid moiety as well. For example, the hydroxyl, methyl, and olefinic groups can be modified to enhance binding affinity to cannabinoid receptors CB1 or CB2. For example, the groups may be modified through acetylation, methylation, or neutralization to form salts. Examples of such derivatives are illustrated in structures (CM-1) through (CM-5):

(CM-1)

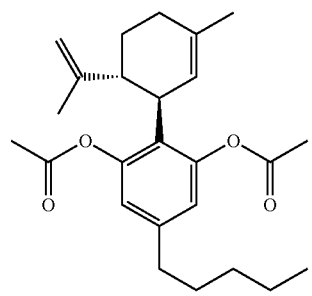

(CM-2)

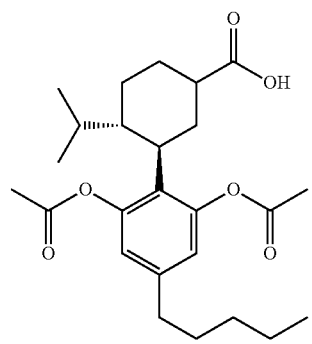

(CM-3)

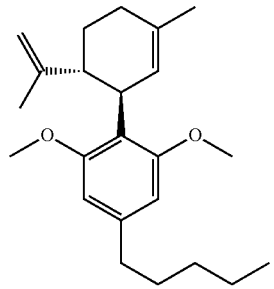

(CM-4)

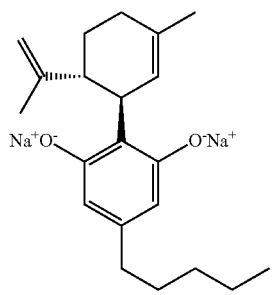

(CM-5)

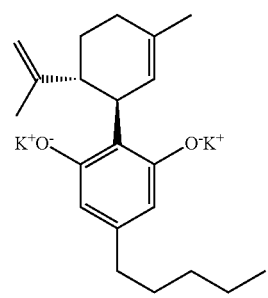

The hydroxyl groups in derivatives (CM-1) and (CM-2) are acetylated, and (CM-2) is also carboxylated. The hydroxyl groups in derivative (CM-3) have been methylated. The sodium and potassium salts of CBD are illustrated in derivatives (CM-4) and (CM-5). Other salts, such as lithium or cesium, are also contemplated.

In some particular embodiments, the linker of Formula (I) has the structure of Formula (L-1):

Formula (L-1)

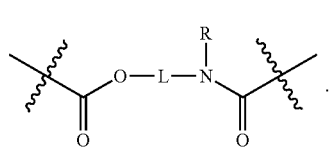

The wiggly lines indicate the presence of a covalent bond. It can be seen that the linker of Formula (L-1) includes an ester end group on the left side, and an amide end group on the right side. The resulting conjugate molecule has the structure of Formula (I-a):

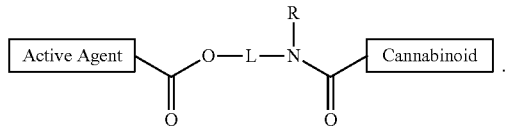

Formula (I-a)

In some particular embodiments, the active agent is a celecoxib moiety, and the cannabinoid moiety is a cannabidiol (CBD) moiety. Conjugate molecules of this structure are illustrated in Formula (II) below:

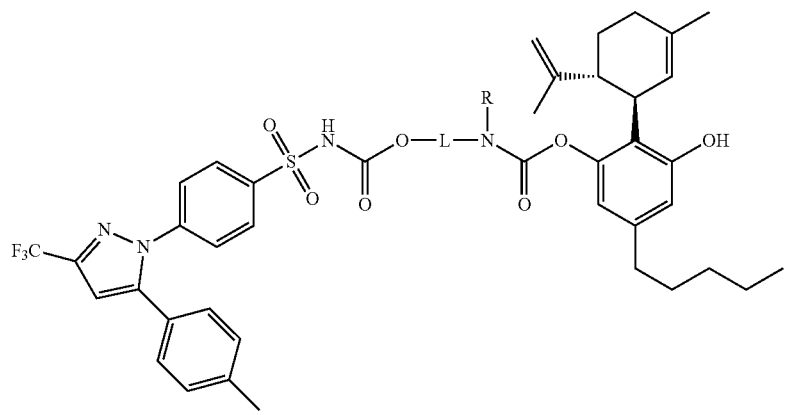

Formula (II)

wherein L is alkyl or substituted alkyl; and wherein R is hydrogen, alkyl, or substituted alkyl. The celecoxib moiety is on the left-hand side of Formula (II), and the CBD moiety is on the right-hand side of Formula (II). The linker contains an ester group which is covalently bonded to the nitrogen atom in the amino group of the celecoxib moiety. The linker also contains an amide group which is covalently bonded to an oxygen atom of the CBD moiety.

The term "alkyl" refers to a radical composed entirely of carbon atoms and hydrogen atoms which is fully saturated. The alkyl radical may be linear, branched, or cyclic. The alkyl radical has the ability to form a single bond to one or two different non-hydrogen atoms, depending on the context. For example, the formulas —$CH_2$—$CH_3$ and —$CH_2$—$CH_2$— should both be considered alkyl. As used herein, an alkyl group has from 1 to about 8 carbon atoms.

The term "amino" refers to a radical of the formula —$NR^1R^2$, where $R^1$ and $R^2$ are independently hydrogen, alkyl, or substituted alkyl. This includes monosubstituted radicals (i.e. where $R^2$ is hydrogen) and disubstituted radicals (where neither $R^1$ nor $R^2$ are hydrogen).

The term "heteroatomic" refers to the end group containing at least one oxygen, nitrogen, or sulfur atom.

The term "ester" refers to a radical of the formula —O—CO—.

The term "amide" refers to a radical of the formula —CO—NR—, where R is hydrogen, alkyl, or substituted alkyl.

The term "substituted" refers to at least one hydrogen atom on the named radical being substituted with another functional group. An exemplary substituted alkyl group is a perhaloalkyl group, wherein one or more hydrogen atoms in an alkyl group are replaced with halogen atoms. An alkyl group can be substituted with a hydroxyl or halogen group.

The term "hydroxyl" refers to —OH.

The term "halogen" refers to fluorine, chlorine, bromine, and iodine.

The term "carboxylic acid" refers to a radical of the formula —COOH. Although the carboxylic acid contains a hydroxyl group, they participate in reactions differently, and so a carboxylic acid group should not be considered a hydroxyl group, and a hydroxyl group should not be considered a carboxylic acid group.

Referring to Formula (II), as previously indicated, L is alkyl containing from 1 to about 8 carbon atoms. In more particular embodiments, L contains 3 to 5 carbon atoms, and in an even more specific embodiment is n-propyl (i.e. 3 carbon atoms arranged linearly).

In more specific embodiments, the conjugate molecule has the structure of Formula (II-a):

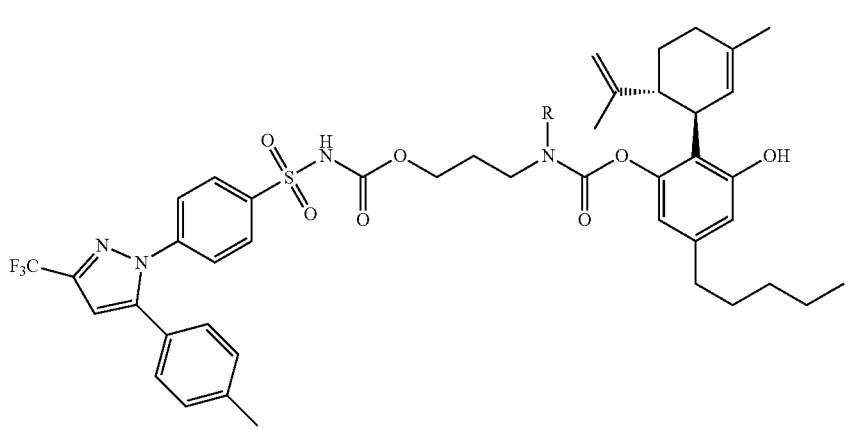

Formula (II-a)

wherein R is hydrogen or alkyl. In particular embodiments, R is alkyl containing from 1 to about 8 carbon atoms. In more particular embodiments, L contains 1 to 3 carbon atoms, and in an even more specific embodiment is a methyl group (—CH$_3$).

In even more specific embodiments, the conjugate molecule has the structure of Formula (III-a) or Formula (III-b):

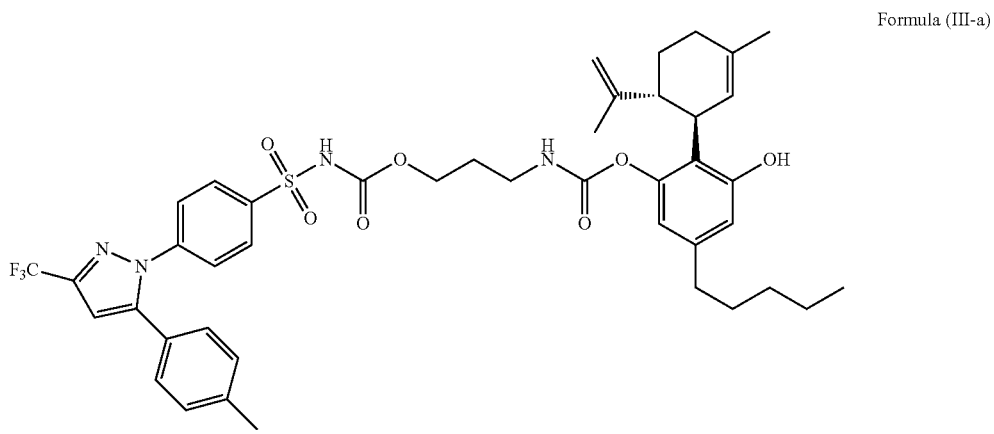

Formula (III-a)

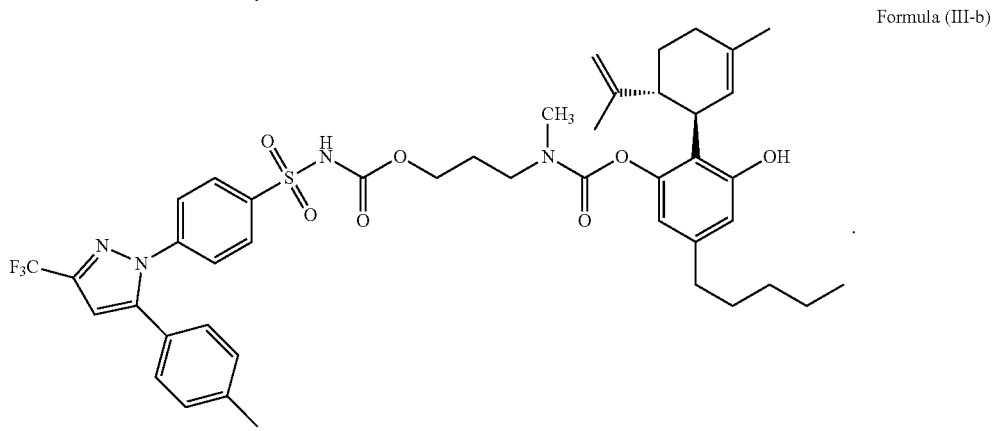

Formula (III-b)

The conjugate molecules of Formula (III-a) and (III-b) correspond to the molecule of Formula (II) when L is n-propyl, and where R is either hydrogen or methyl.

Non-limiting examples of conjugate molecules containing other cannabinoid derivatives are illustrated below in Formulas (IV-a) through (IV-c):

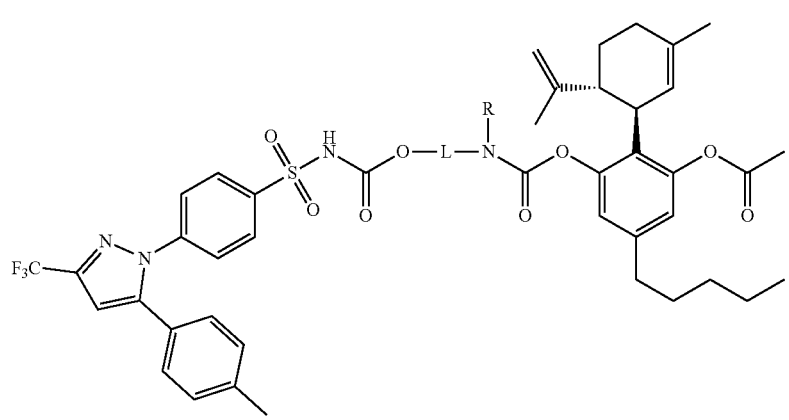

Formula (IV-a)

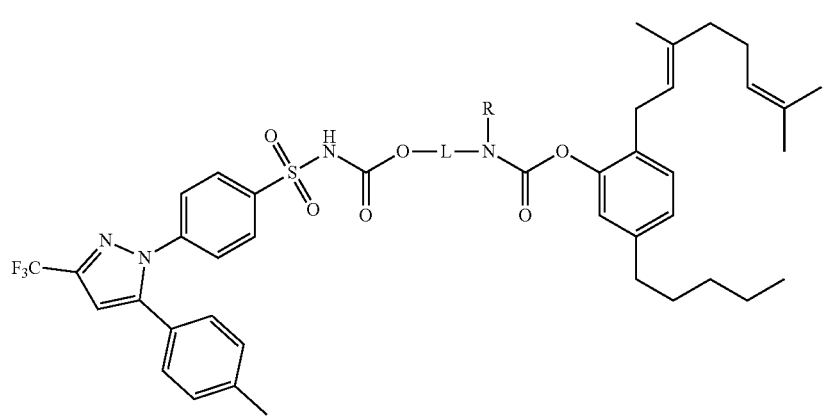

Formula (IV-b)

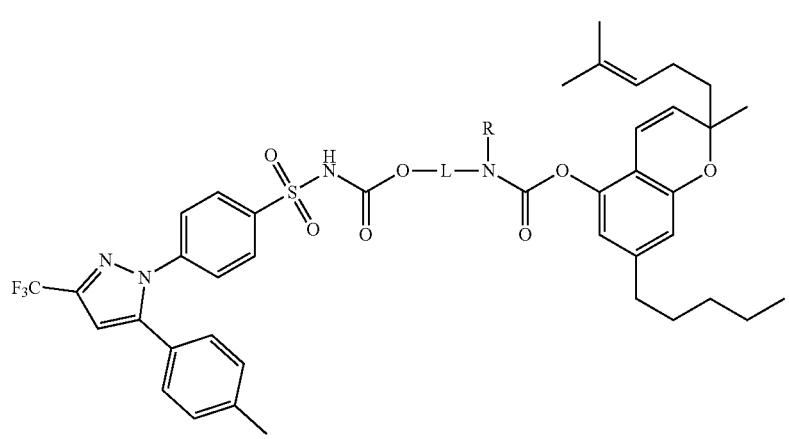

Formula (IV-c)

wherein L is alkyl or substituted alkyl; and wherein R is hydrogen, alkyl, or substituted alkyl.

In these three formulas, the active agent is illustrated as a celecoxib moiety. In Formula (IV-a), the cannabinoid moiety is the acetylated derivative (CM-1), now mono-acetylated or having an acetoxy substituent. The derivatives of (CM-2)-(CM-5) can also be used. In Formula (IV-b), the cannabinoid moiety is cannabigerol, and in Formula (IV-c), the cannabinoid moiety is cannabichromene. Again, these are examples, and different cannabinoids and derivatives may be used in the conjugate molecules of the present disclosure.

Synthesis

Figure 1B:
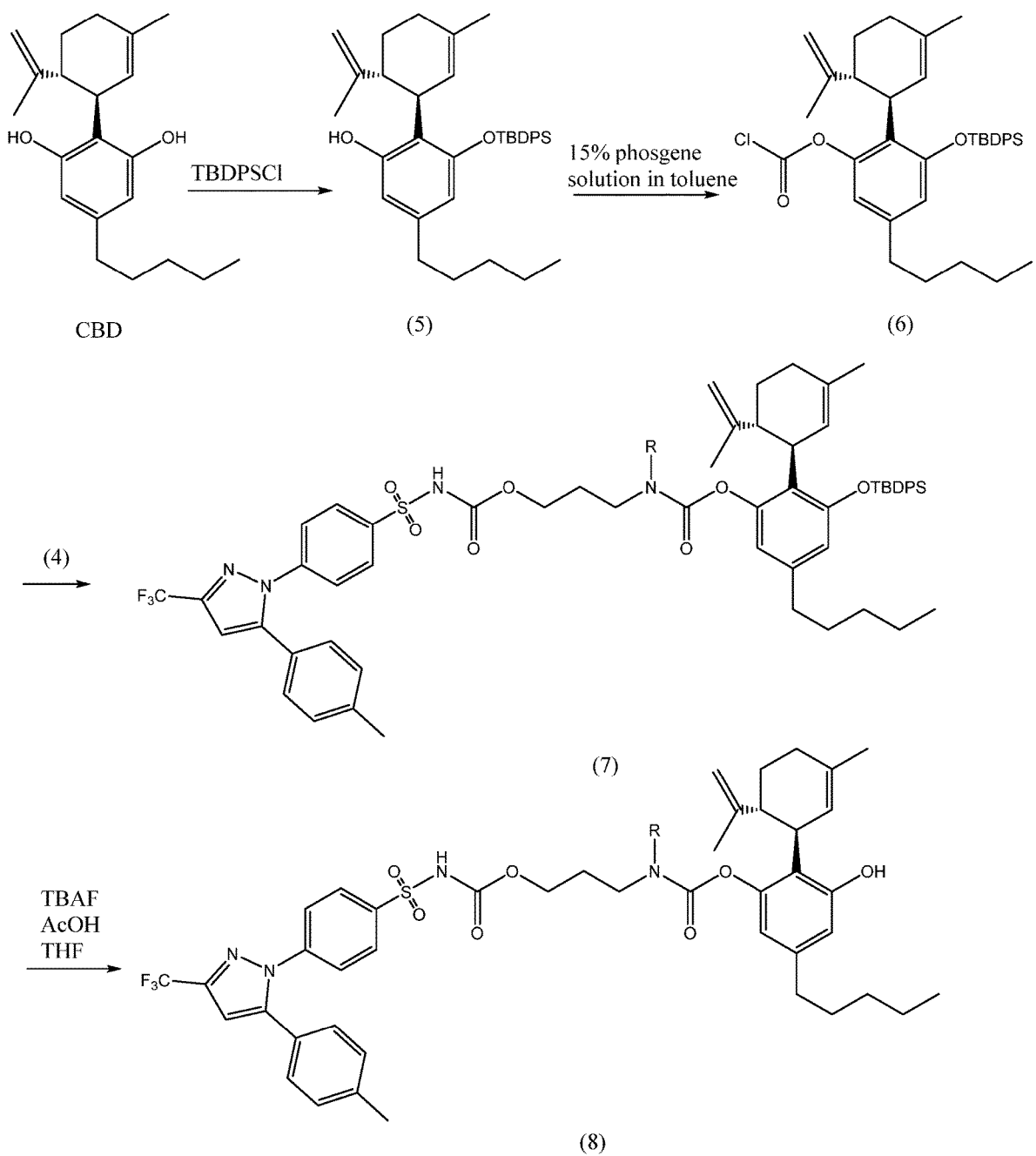
FIG. 1B is the second part of a synthetic route for preparing a conjugate molecule, in some embodiments.

The conjugate molecules of the present disclosure, containing a cannabinoid moiety and a COX-2 inhibitor moiety, can be synthesized using methods known in the art. FIG. 1A and FIG. 1B illustrate one method for synthesizing the molecules of Formula (II), using the conjugate molecules of Formula (III-a) and Formula (III-b) as an example.

Referring first to FIG. 1A, molecule 1 is a 3-aminopropan-1-ol (or more broadly, an aminohydroxyalkane) in which one hydrogen atom on the amino group has been replaced with a t-butyloxycarbonyl (Boc) protecting group. It is noted that the molecule 1 must have at least one hydrogen atom. Again, R can be hydrogen, alkyl, or substituted alkyl. The addition of the Boc protecting group is typically performed in a solvent such as water, water/THF, THF, acetonitrile, dioxane, or methanol at room temperature or moderate heat (40° C.) in the presence of a base. Common bases include sodium hydroxide, 4-dimethylaminopyridine (DMAP) and sodium bicarbonate.

When reacted with phosgene, the hydroxyl group is converted to a chloroformate group to form first intermediate molecule 2, a 3-aminopropyl chloroformate, or more generally an aminoalkyl chloroformate. The first intermediate molecule 2 is then reacted with celecoxib (or more broadly, an active agent having an acidic hydrogen atom attached to a nitrogen atom). The chloroformate group of molecule 2 reacts with the amino group of the celecoxib molecule, forming a covalent bond and releasing HCl in the process to obtain second intermediate molecule 3. The Boc protecting group is then removed to obtain primary intermediate molecule 4. The removal is performed in an acidic environment in water or an organic solvent such as toluene, dichloromethane, or ethyl acetate. Concentrated hydrochloric acid (HCl) or trifluoroacetic acid (TFA) can be used. The reaction usually occurs at room temperature.

Referring now to FIG. 1B separately, the cannabinoid broadly contains at least one hydroxyl group. As illustrated here, CBD is reacted with TBDPSCl (t-butyl-diphenylchlorosilane) to replace the hydrogen atom on one of the hydroxyl groups with a TBDPS protecting group and obtain third intermediate molecule 5. Next, third intermediate molecule 5 is reacted with phosgene to convert the second hydroxyl group to a chloroformate group to obtain secondary intermediate molecule 6. The use of the protecting group is optional, with the recognition that the resulting conjugate molecule will not correspond to the structure Formula (II) because both hydroxyl groups are free to react in subsequent steps.

Continuing, primary and secondary intermediate molecules 4 and 6 are then reacted with each other to form tertiary intermediate molecule 7. The chloroformate group of molecule 6 reacts with the amino group of molecule 4, forming a covalent bond and releasing HCl again. The tertiary intermediate molecule 7 is then reacted with TBAF (tetra-n-butylammonium fluoride) and AcOH (acetic acid) in THF (tetrahydrofuran) to remove the TBDPS protecting group, resulting in the molecule of Formula (II), which is labeled 8 in FIG. 1B.

The method described in these two figures can be modified, for example, by changing the starting products, to obtain the desired final conjugate molecule. For example, cimicoxib, polmacoxib, valdecoxib, and bromfenac each contain the same primary amino group as celecoxib, and so the reaction of FIG. 1A and FIG. 1B can apply. As another example the chloroformate group of the first intermediate molecule 2 will also react with a secondary amino group and a carboxylic acid group as are present in lumiracoxib, parecoxib, bromfenac, etodolac, ketorolac tromethamine, meloxicam, and oxaprozin. The term "conjugate molecule" should be construed as also including the molecule in the form of a salt, for example by replacing a hydrogen atom with a metal ion such as sodium (Na) or potassium (K).

More generally, then, a method for synthesizing a conjugate molecule of the present disclosure begins with an aminoalkyl chloroformate having a protecting group on the amino group (e.g. the first intermediate molecule 2). In this molecule, the amino group and the chloroformate group are at opposite ends of the alkyl chain. The aminoalkyl chloroformate is then reacted with an active agent having an acidic hydrogen atom attached to a nitrogen atom. A covalent bond is formed between the chloroformate and the nitrogen atom to obtain a second intermediate molecule. The protecting group is removed from the amino group to obtain a primary intermediate molecule comprising the active agent. A secondary intermediate molecule comprising a cannabinoid having a chloroformate group is then reacted the primary intermediate molecule with the secondary intermediate molecule to obtain the conjugate molecule.

The secondary intermediate molecule can prepared by reacting a cannabinoid with, for example, TBDPSCl, to form a protecting group on a hydroxyl group of the cannabinoid and obtain the secondary intermediate molecule. This controls the reaction between the primary intermediate molecule and the secondary intermediate molecule. The protecting group on the secondary intermediate molecule can then be removed from the conjugate molecule.

Figure 1C:
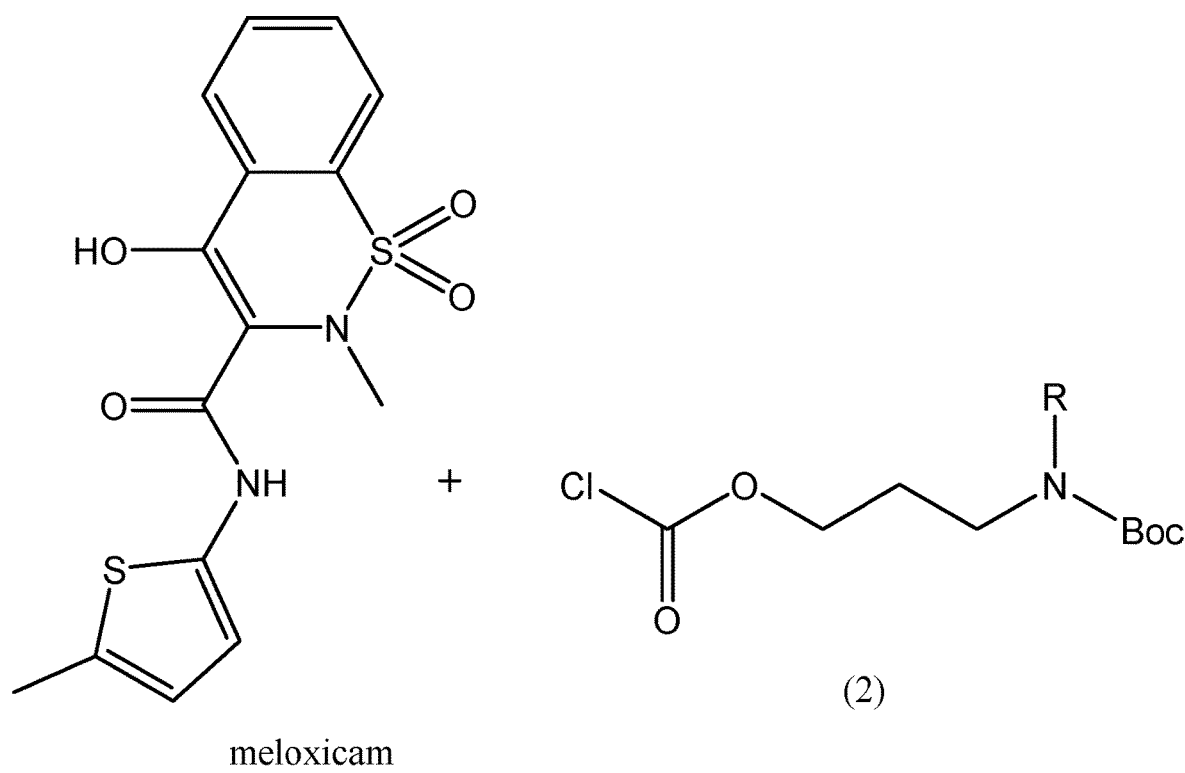
FIG. 1C is an illustration of a modified part of the synthetic route for preparing a conjugate molecule, in some embodiments.
Figure 1C:
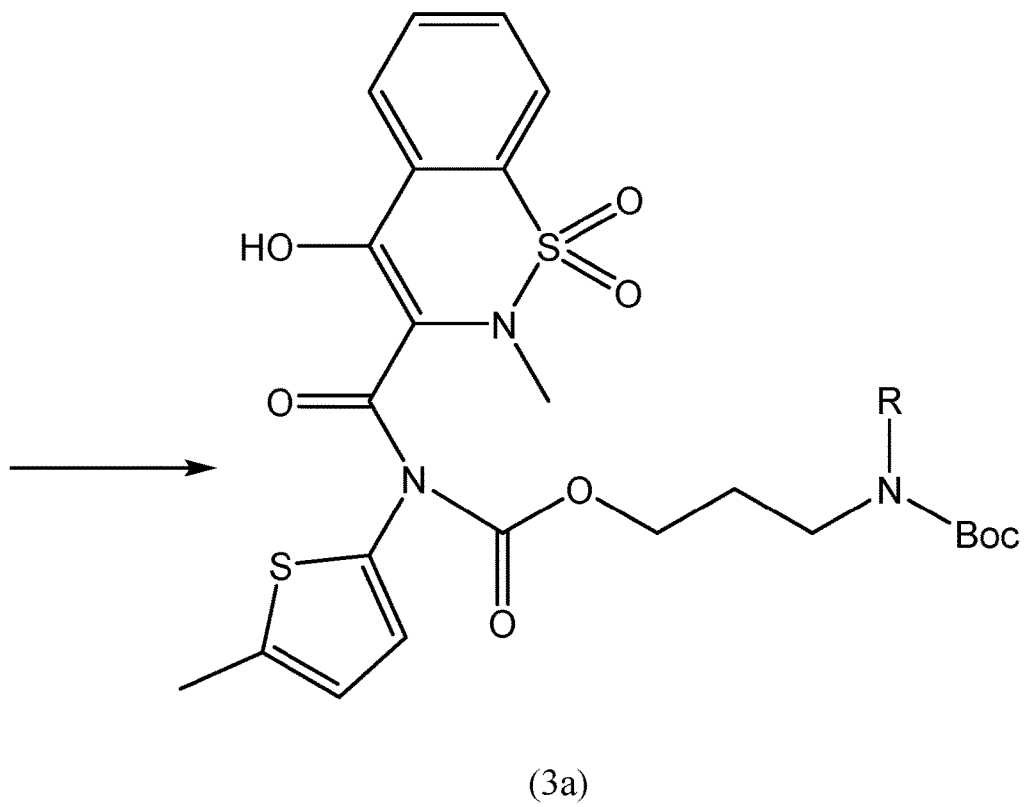

FIG. 1C illustrates what is believed to be a general reaction between the first intermediate molecule 2 and a secondary amide group, illustrated here using meloxicam to obtain a second intermediate molecule 3a. The conjugate molecule can then be formed continuing the process as illustrated in FIG. 1A and FIG. 1B.

Figure 1D:
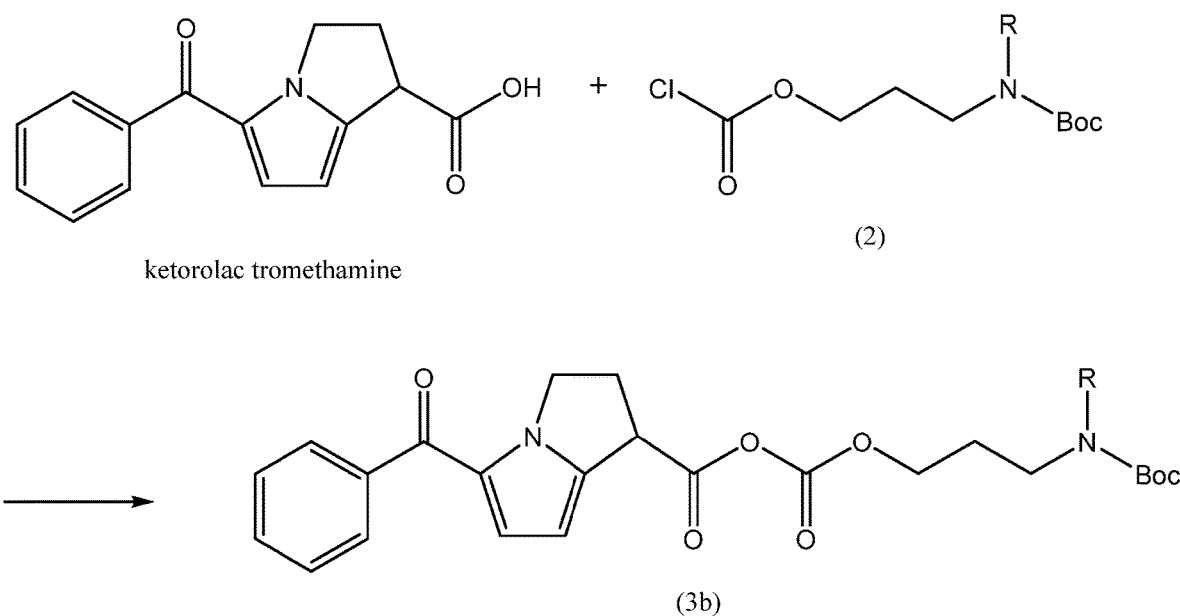
FIG. 1D is another illustration of a modified part of the synthetic route for preparing a conjugate molecule, in some embodiments.

FIG. 1D illustrates what is believed to be a general reaction between the first intermediate molecule 2 and a carboxylic acid chloride group, illustrated here using ketorolac tromethamine to obtain a second intermediate molecule 3b. The conjugate molecule can then be formed continuing the process as illustrated in FIG. 1A and FIG. 1B.

Figure 1E:
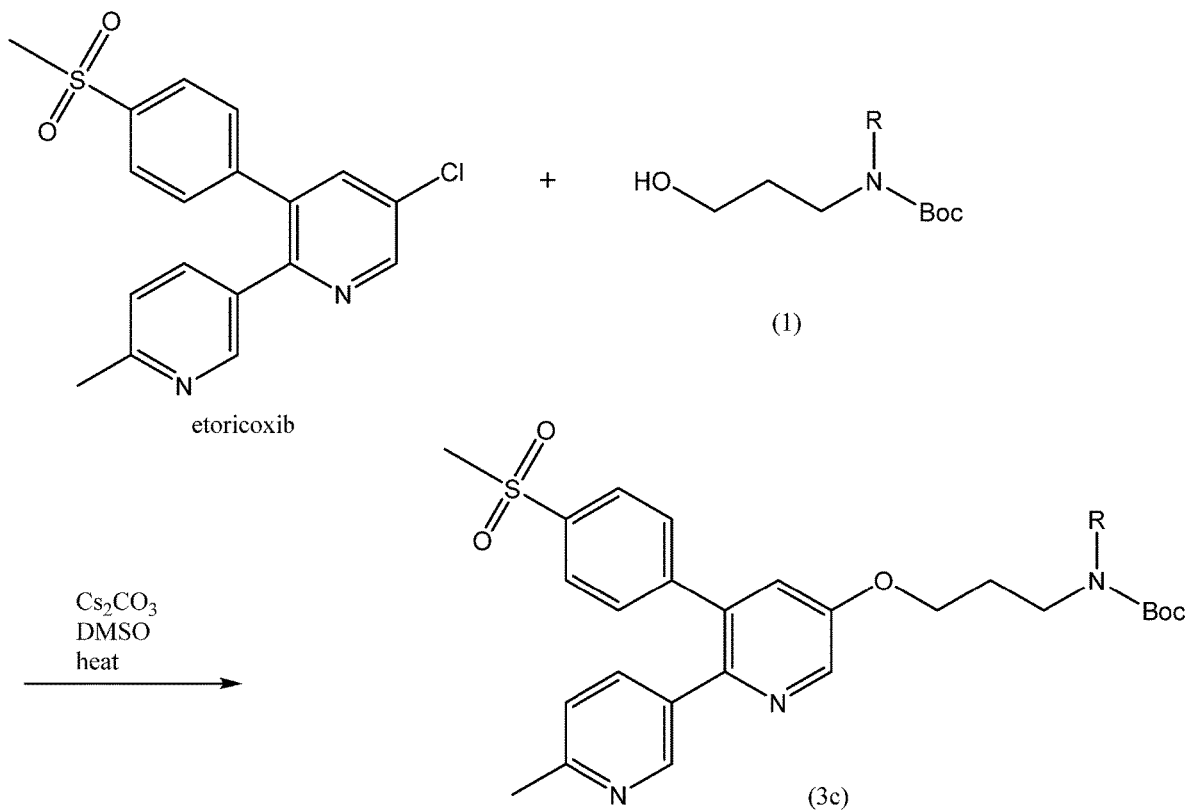
FIG. 1E is another illustration of a modified part of the synthetic route for preparing a conjugate molecule, in some embodiments.

FIG. 1E illustrates what is believed to be a first general reaction for obtaining a second intermediate molecule for etoricoxib. Etoricoxib is reacted with protected aminohydroxyalkane 1 in the presence of cesium carbonate, dimethyl sulfoxide (DMSO), and heat to obtain second intermediate molecule 3c. Notably, the aminohydroxyalkane reacts with the chloride atom instead of a nitrogen atom. The conjugate molecule can then be formed continuing the process as illustrated in FIG. 1A and FIG. 1B.

Figure 1F:
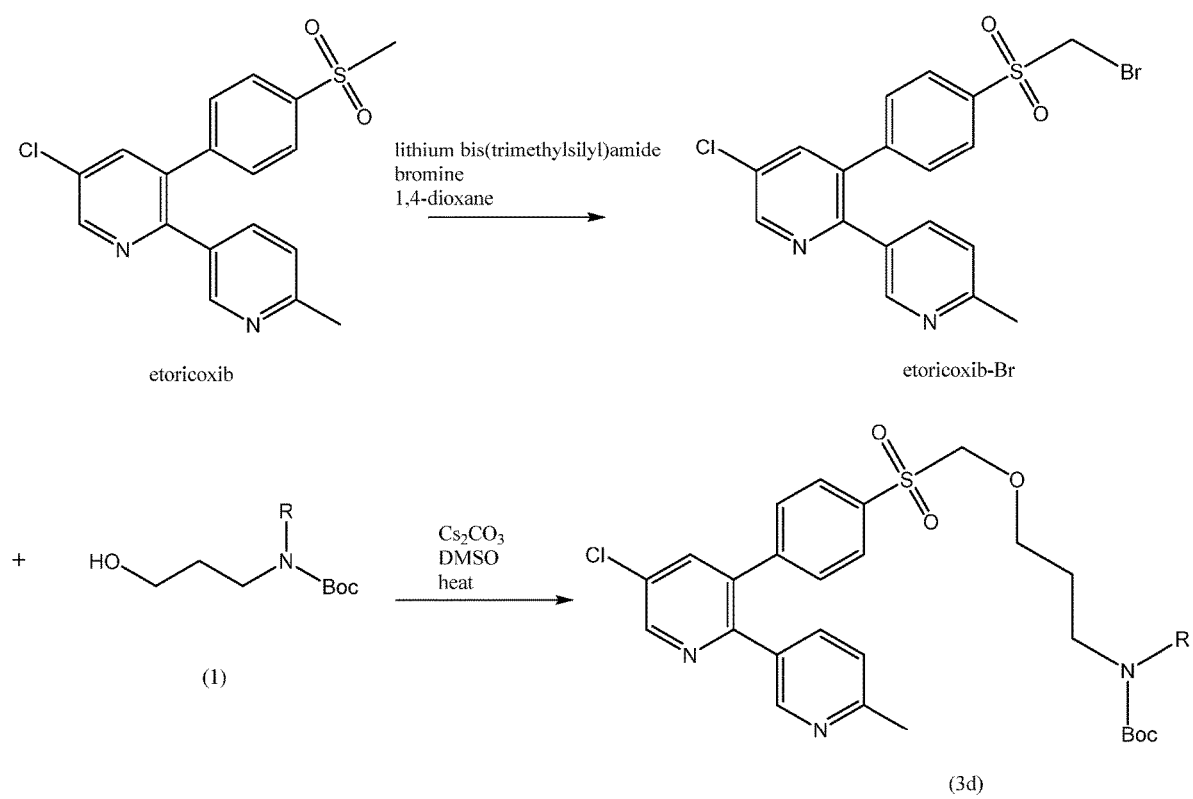
FIG. 1F is another illustration of a modified part of the synthetic route for preparing a conjugate molecule, in some embodiments.

FIG. 1F illustrates what is believed to be a second general reaction for obtaining a second intermediate molecule for etoricoxib. Etoricoxib is first reacted in the presence of lithium bis(trimethylsilyl)amide, bromine, and 1,4-dioxane to obtain what is labeled here as etoricoxib-Br. This molecule includes a bromine atom on the methyl group next to the sulfonyl group. The etoricoxib-Br is then reacted with protected aminohydroxyalkane 1 in the presence of cesium carbonate, dimethyl sulfoxide (DMSO), and heat to obtain second intermediate molecule 3d. Here, the aminohydroxyalkane reacts with the bromine atom. The conjugate molecule can then be formed continuing the process as illustrated in FIG. 1A and FIG. 1B.

Figure 1G:
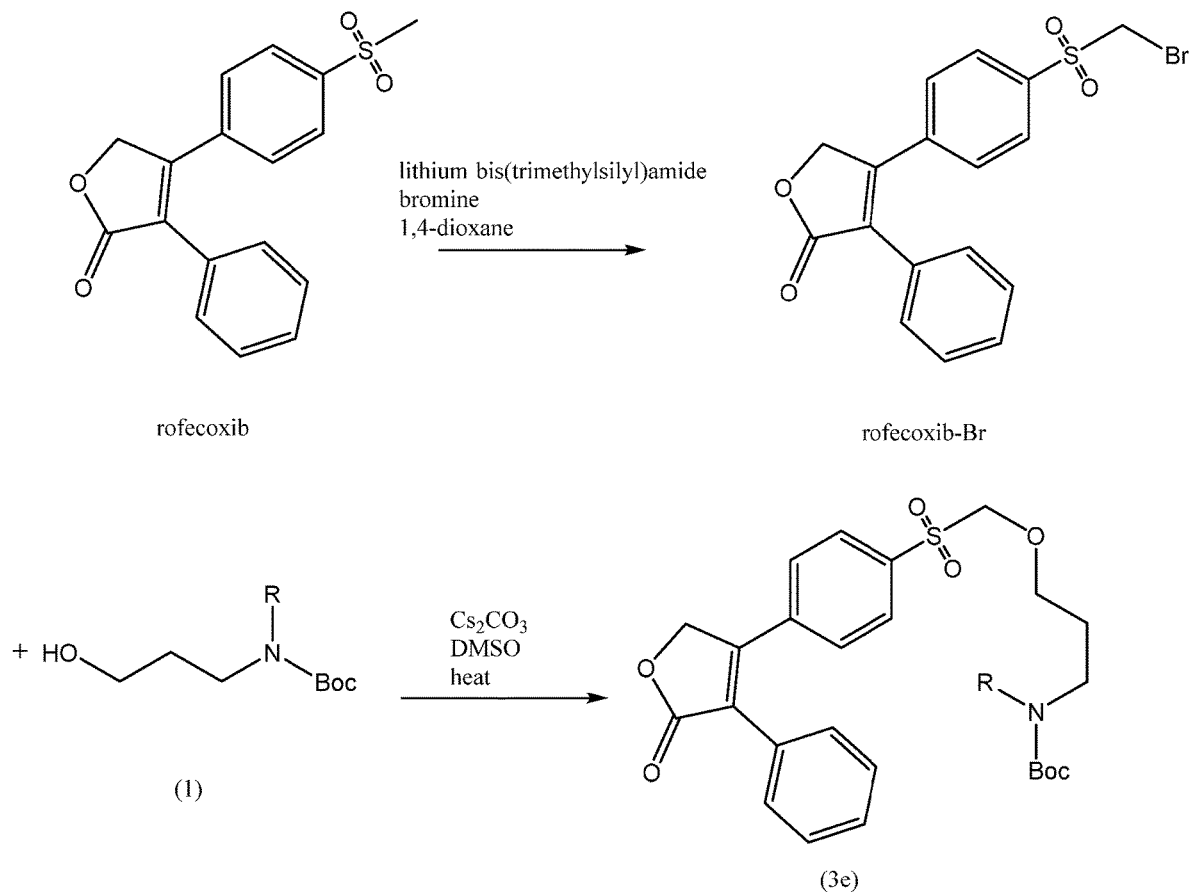
FIG. 1G is another illustration of a modified part of the synthetic route for preparing a conjugate molecule, in some embodiments.

FIG. 1G illustrates what is believed to be a general reaction for obtaining a second intermediate molecule for rofecoxib. This reaction is essentially the same as that illustrated in FIG. 1F, but using rofecoxib instead of etoricoxib. The first intermediate is labeled here as rofecoxib-Br, which is then reacted with protected aminohydroxyalkane 1 to obtain second intermediate molecule 3e. The conjugate molecule can then be formed continuing the process as illustrated in FIG. 1A and FIG. 1B.

Figure 1H:
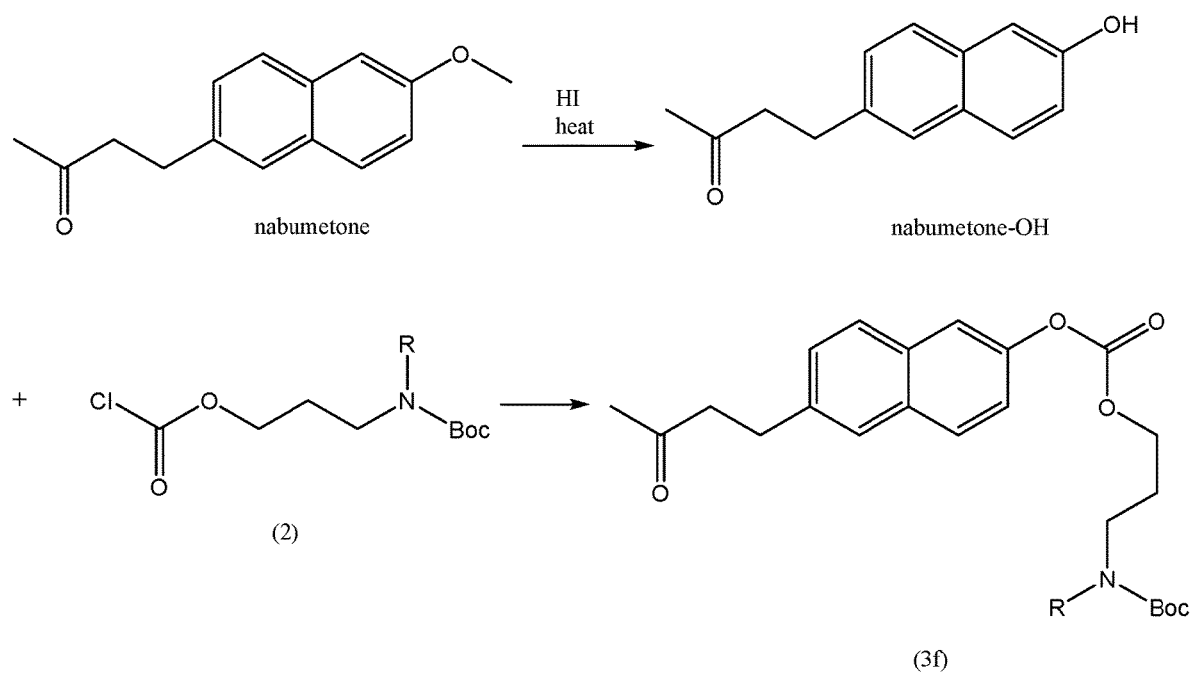
FIG. 1H is another illustration of a modified part of the synthetic route for preparing a conjugate molecule, in some embodiments.

FIG. 1H illustrates what is believed to be a general reaction for obtaining a second intermediate molecule using nabumetone. Nabumetone is reacted in the presence of hydrogen iodide and heat to replace the methoxy group with a hydroxyl group, obtaining a molecule that is labeled here as nabumetone-OH. The nabumetone-OH is then reacted with the first intermediate molecule 2 to obtain second intermediate molecule 3f. The conjugate molecule can then be formed continuing the process as illustrated in FIG. 1A and FIG. 1B.

In situations where the COX-2 inhibitor moiety has multiple reactive groups, protecting groups may be applied to direct the reaction towards only one of the reactive groups. For example, lumiracoxib, bromfenac, and etodolac each have an amino group and a carboxylic acid group. An appropriate protecting group could be applied, for example, to the amino group to direct the reaction of the first intermediate molecule 2 towards the carboxylic acid group, or vice versa. The protecting group could then be removed at an appropriate step in the synthesis of the conjugate molecule.

The term "conjugate molecule" should be construed as also including the molecule in other forms such as a salt, for example by replacing a hydrogen atom with a metal ion such as sodium (Na) or potassium (K), or an acid, an ester, an analog, or a derivative.

Applications

The conjugate molecules of the present disclosure can be used in a pharmaceutical composition suitable for being administered to a subject such as a human or animal. The composition should contain a pharmaceutically effective amount of the conjugate molecule. In particular embodiments, the pharmaceutically effective amount may range from about 0.1 to about 1000 milligrams per milliliter of the composition (w/v).

The pharmaceutical composition may be administered via topical, transdermal, oral, nasal, intravenous, intra-arterial, intradermal, subcutaneous, intramuscular, intravenous, intraperitoneal, intrapleural, vaginal, intraurethral, intratumoral, intravesicular, intrathecal, intracranial, intraspinal, sublingual, buccal, or rectal routes, as appropriate or feasible for the given medical condition. The dose used in a particular formulation or application may be determined by the requirements of the particular state of disease and the constraints imposed by the characteristics or capacities of the carrier materials. It contemplated in that in the most desirable form, the composition will be administered topically.

The pharmaceutical composition may include a pharmaceutically acceptable carrier. The carrier acts as a vehicle for delivering the conjugate molecule. Examples of pharmaceutically acceptable carriers include liquid carriers like water, oil, and alcohols, in which the conjugate molecule can be dissolved or suspended.

The pharmaceutical composition may also include excipients. Particular excipients include buffering agents, surfactants, preservative agents, bulking agents, polymers, and stabilizers, which are useful with these molecular antagonists. Buffering agents are used to control the pH of the composition. Surfactants are used to stabilize proteins, inhibit protein aggregation, inhibit protein adsorption to surfaces, and assist in protein refolding. Exemplary surfactants include Tween 80, Tween 20, Brij 35, Triton X-10, Pluronic F127, and sodium dodecyl sulfate. Preservatives are used to prevent microbial growth. Examples of preservatives include benzyl alcohol, m-cresol, and phenol. Bulking agents are used during lyophilization to add bulk. Hydrophilic polymers such as dextran, hydroxyl ethyl starch, polyethylene glycols, and gelatin can be used to stabilize proteins. Polymers with nonpolar moieties such as polyethylene glycol can also be used as surfactants. Protein stabilizers can include polyols, sugars, amino acids, amines, and salts. Suitable sugars include sucrose and trehalose. Amino acids include histidine, arginine, glycine, methionine, proline, lysine, glutamic acid, and mixtures thereof. Proteins like human serum albumin can also competitively adsorb to surfaces and reduce aggregation of the protein-like molecular antagonist. It should be noted that particular molecules can serve multiple purposes. For example, histidine can act as a buffering agent and an antioxidant. Glycine can be used as a buffering agent and as a bulking agent.

The pharmaceutical composition may be in the form of a powder, injection, solution, suspension, or emulsion. It is more particularly contemplated that the composition will be delivered by injection or by topical administration. The conjugate molecule may be lyophilized using standard techniques known to those in this art. The lyophilized conjugate molecule may then be reconstituted with, for example, suitable diluents such as normal saline, sterile water, glacial acetic acid, sodium acetate, combinations thereof and the like.

Dose will depend on a variety of factors, including the therapeutic index of the drugs, disease type, patient age, patient weight, and tolerance. The dose may broadly be chosen to achieve serum concentrations from about 0.1 μg/ml to about 100 μg/ml in the patient. The dose of a particular patient can be determined by the skilled clinician using standard pharmacological approaches in view of the above factors. The response to treatment may be monitored by analysis of blood or body fluid levels of the patient, or by other appropriate means. The skilled clinician will adjust the dose based on the response to treatment revealed by these measurements. A single administration may usually be sufficient to produce a therapeutic effect, but it is contemplated that multiple administrations will be used to assure continued response over a substantial period of time.

The pharmaceutical compositions of the present disclosure can be used to treat any appropriate medical condition. The term "treat" is used to refer to a reduction in progression of the medical condition, a regression in the medical condition, and/or a prophylactic usage to reduce the probability of presentation of the medical condition. Such medical conditions might include inflammatory conditions such as arthritis, or pain management, or cancer, or neuropsychiatric disorders. This may include any form of arthritis, such as osteoarthritis, rheumatoid arthritis, ankylosing spondylitis, or gout, whether in adult or juvenile patients. Non-limiting examples of pain that could be treated might include acute pain, painful menstruation, or pain after surgery. Non-limiting examples of cancers include colorectal adenomas, pre-cancerous growths, familial adenomatous polyposis, neuroblastoma, or breast cancer. Any neuropsychiatric disorder might be treatable, including for example major depressive disorder or schizophrenia.

Additional examples of medical conditions for which some COX-2 inhibitors have been approved for use include acute and sub-acute bursitis; age related macular degeneration; allergic conjunctivitis; ankylosing spondylitis (Bekhterev's disease); anterior segment inflammation; anterior uveitis; arthritis pain; back pain; blepharitis; cancer pain; colorectal cancer; conjunctivitis; cystoid macular edema; dental abscess; dental pain (toothache/tooth pain); depression; dysmenorrhea; familial adenomatous polyposis; frozen shoulder syndrome; gouty arthritis (gout); juvenile arthritis; juvenile rheumatoid arthritis; low back pain; migraine; myalgia (muscle pain); ocular inflammation; ocular pain (eye pain); osteoarthritis; osteoarthritis pain; pain; polyarticular arthritis; post-operative pain; primary dysmenorrhea; renal colic; rheumatoid arthritis; rheumatoid arthritis pain; schizophrenia; scleritis; tendon and ligament pain; tenosynovitis; traumatic pain; and visceral pain.

In particular embodiments, the pharmaceutical compositions/formulations of the present disclosure are intended to be applied topically to the skin of the user/patient. This results in the active ingredient being delivered to local tissue. The formulations may also operate transdermally, delivering the active ingredient across the skin and into systemic circulation.

The topical formulation may be in the form of a cream, gel, hydrogel, liquid, lotion, or ointment. The topical formulation may be applied manually, sprayed, or by syringe, applicator, or other dispensing means. The topical formulation could alternatively be provided in the form of a matrix-type delivery system, where the formulation is absorbed or suspended in a matrix that is then adhered to a backing membrane (commonly referred to as a bandage or a patch).

The conjugate molecules of the present disclosure may be administered singly, or in combination with other pharmaceutical therapies. For example, the pharmaceutical composition may also contain a second therapeutic agent which operates by a distinct mechanism of action or through another pathway. For example, for pain management applications, the second therapeutic agent could include acetaminophen; a non-steroidal anti-inflammatory drug (NSAID) such as aspirin, ibuprofen, or naproxen; a COX-2 inhibitor; or an opioid such as codeine, oxycodone, hydrocodone, buprenorphine, or tramadol. In such embodiments, it is further contemplated that the conjugate molecule and the second therapeutic agent are individually present in less-than-pharmaceutically effective amounts, but together obtain the desired therapeutic effect, and might act together synergistically as well.

The present disclosure, in a further aspect, includes providing a kit comprising a pharmaceutical composition as described above, which may also contain any or all of an applicator, such as a pad, utensil, spatula, sprayer or droplet dispenser; and/or a bandage, such as a dermal patch, wrap or other form of bandage and instructions for use thereof.

The following examples are provided to illustrate various aspects of the molecules and methods of the present disclosure. The examples are merely illustrative and are not intended to limit the disclosure to the materials, conditions, or process parameters set forth therein.

EXAMPLES

Example 1

The conjugate molecule of Formula (III-a) was made.

Referring to FIG. 1A, where R is hydrogen, 3-t-butoxycarbonylamino-1-propanol (1) (1.03 grams, 5.88 mmol) in a dichloromethane (DCM) solution was reacted with a phosgene solution (5.04 grams, 5.47 mL) at 0° C. Anhydrous pyridine (1.4 grams) was slowly added. The mixture was kept at 0° C. for 1 hour to obtain the chloroformate (2). Celecoxib (1.34 grams, 3.5 mmol) was then added. The mixture was returned to room temperature overnight. A yellow solution and white solid was obtained. A mixture of deionized water and DCM was added, and the organic phase was collected and concentrated, then run through a column to obtain the second intermediate molecule (3) (800 mg). The identity of (3) was verified using NMR.

The second intermediate molecule (3) was mixed with 1N HCl in ethyl acetate (3 mL) at room temperature, but the reaction was very slow, so was rotary evaporated and then switched to 4N HCl in dioxane (3 mL) at room temperature overnight. After additional concentration, the remainder was loaded onto a column to obtain the primary intermediate molecule (4) (480 mg). The identity of (3) was verified using NMR and MS. Further experiments increased the product yield, so that 320 mg of celecoxib would yield 280 mg of the primary intermediate molecule (4).

Next, referring to FIG. 1B, CBD (5.1 grams) was mixed with TBDPS-chloride (10.2 grams) in imidazole (2.7 grams) and anhydrous THF (100 mL) overnight at 60° C. to obtain the third intermediate molecule (5). A mixture of deionized water and ethyl acetate was added, and the organic phase was collected and concentrated, then run through a column with DCM to collect the third intermediate molecule (5) (5.63 grams). The third intermediate molecule (235 mg, 0.425 mmol) was then reacted with phosgene (365 microliters) in anhydrous DCM and pyridine (50 mg), then underwent workup and a chromatographic purification prior to concentration to obtain the secondary intermediate molecule (6) (95 mg). The mixture was rotary evaporated to dryness.

The primary intermediate molecule (4) (164 mg, 0.34 mmol) was dissolved in DCM (3 mL) and treated with phosgene solution (365 microliters) and pyridine (50 mg). TLC indicated incomplete reaction, so an additional portion of phosgene solution was added (50 microliters) and the reaction mixture was then concentrated to dryness. This was combined with the secondary intermediate molecule (6) (235 mg, 0.425 mmol) and N,N-diisopropylethylamine ($iPr_2NEt$, 175 mg) in anhydrous DMF (5 mL), stirring until completion. The reaction was partitioned between ethyl acetate and deionized water and the organic phase concentrated for purification. Column chromatography with first DCM/MeOH and then heptane/ethyl acetate afforded tertiary intermediate molecule (7) (95 mg). The identity of (7) was verified using NMR and MS. Removal of the TBDPS protecting group was done in TBAF/THF/AcOH at room temperature for about 20 minutes to obtain the conjugate molecule (8) (40 mg).

Further experiments increased the product yield, so that 125 mg of tertiary intermediate molecule (7) yielded 70 mg of the conjugate molecule (8). Purity of up to 95.5% was attained.

Example 2

The conjugate molecule of Formula (III-b) was also made. The procedure was much the same as in Example 1, except the starting molecule (1) was 3-t-butoxycarbonylmethylamino-1-propanol. The identity of the third intermediate molecule (5) was verified using NMR. The identity of (7) was verified using NMR and MS. Purity of up to 96.3% was attained.

Comparative Example 1

Figure 2A:
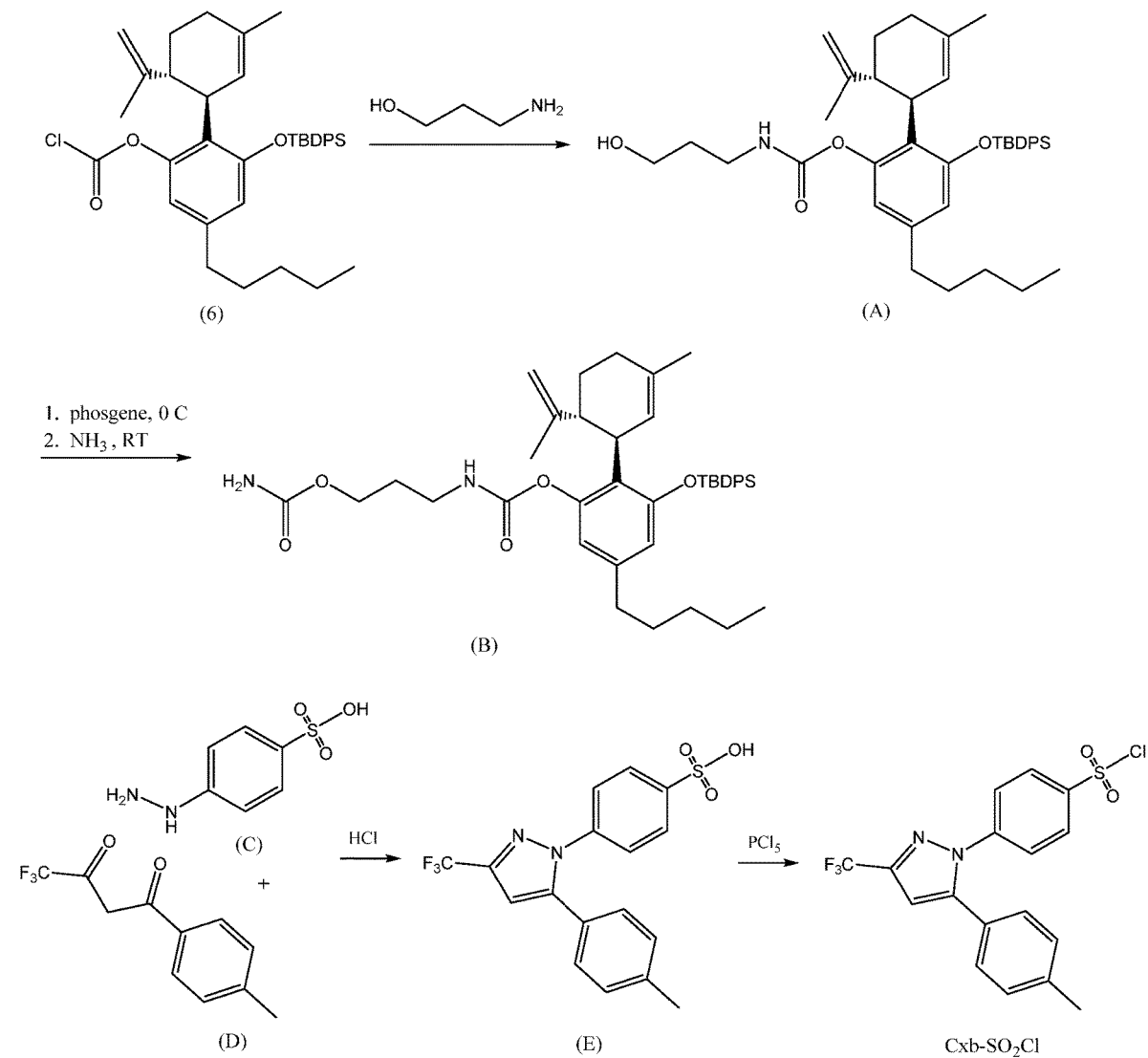
FIG. 2A and FIG. 2B illustrate a first comparative synthetic route which was not successful in producing the desired conjugate molecule.
Figure 2B:
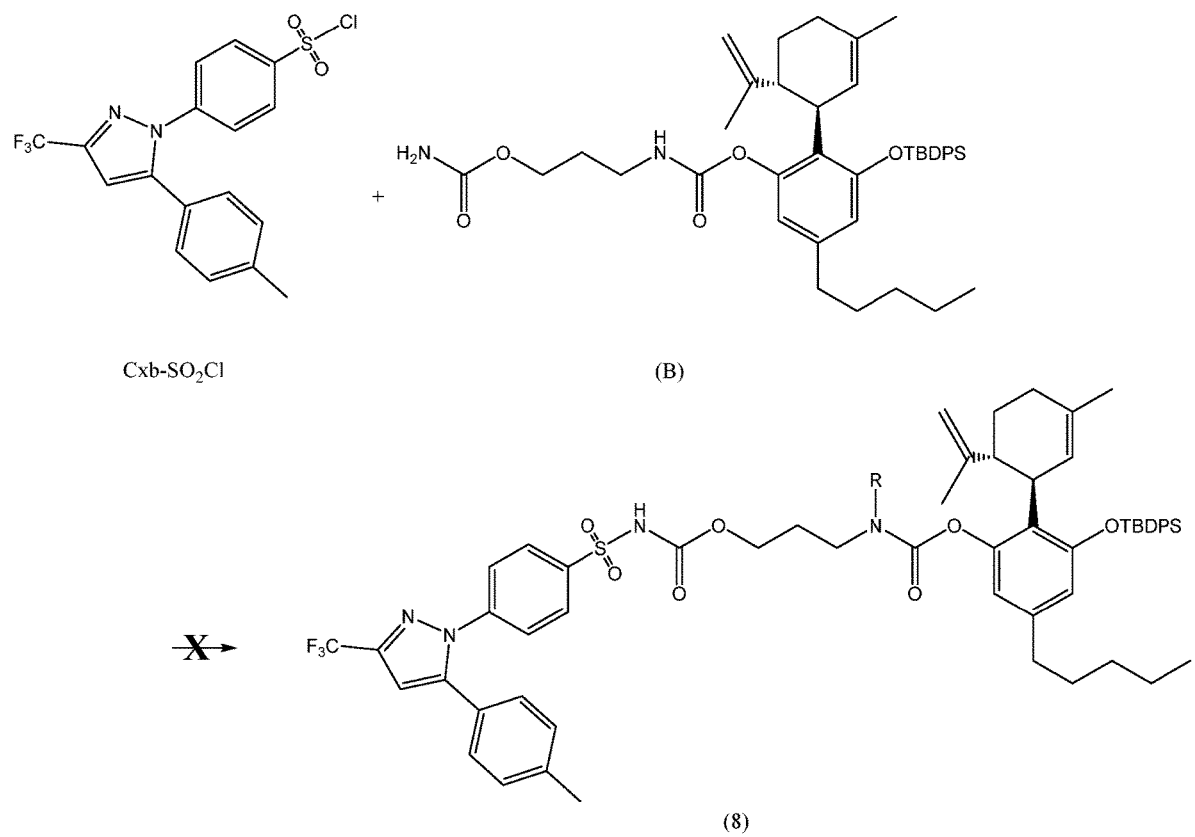

An alternative synthesis reaction was attempted for conjugate molecule (8), as illustrated in FIGS. 2A-2B. Briefly, as designed and as illustrated in FIG. 2A, the CBD chloroformate (6) was reacted with 3-amino-1-propanol to obtain intermediate (A), then reacted with phosgene and ammonia to obtain intermediate (B). Separately, the sulfonyl chloride of celecoxib ($Cxb-SO_2Cl$) was prepared by the reaction of two starting reactants (C, D) in HCl to obtain intermediate (E), then chlorinating with PCl5. Next, in FIG. 2B, intermediate (B) and the $Cxb-So_2Cl$ were then reacted together to obtain the conjugate molecule (8). In FIGS. 2A-2B, then, the linker (formed from the 3-amino-1-propanol) is first attached to the CBD moiety instead of the celecoxib moiety as in FIGS. 1A-1B.

However, in attempting the reaction of intermediate (B) with the $Cxb-So_2Cl$, no reaction occurred. The reaction was run in toluene and pyridine, then DMAP was added, and the mixture was heated, but no reaction was observed. Sodium hydride was added, and no reaction was observed. This is indicated in FIG. 2B with the large X, indicating no product (8) was obtained. Instead, there was evidence that the Cxb-So₂Cl was hydrolyzed to the corresponding sulfonic acid.

Comparative Example 2

Figure 3:
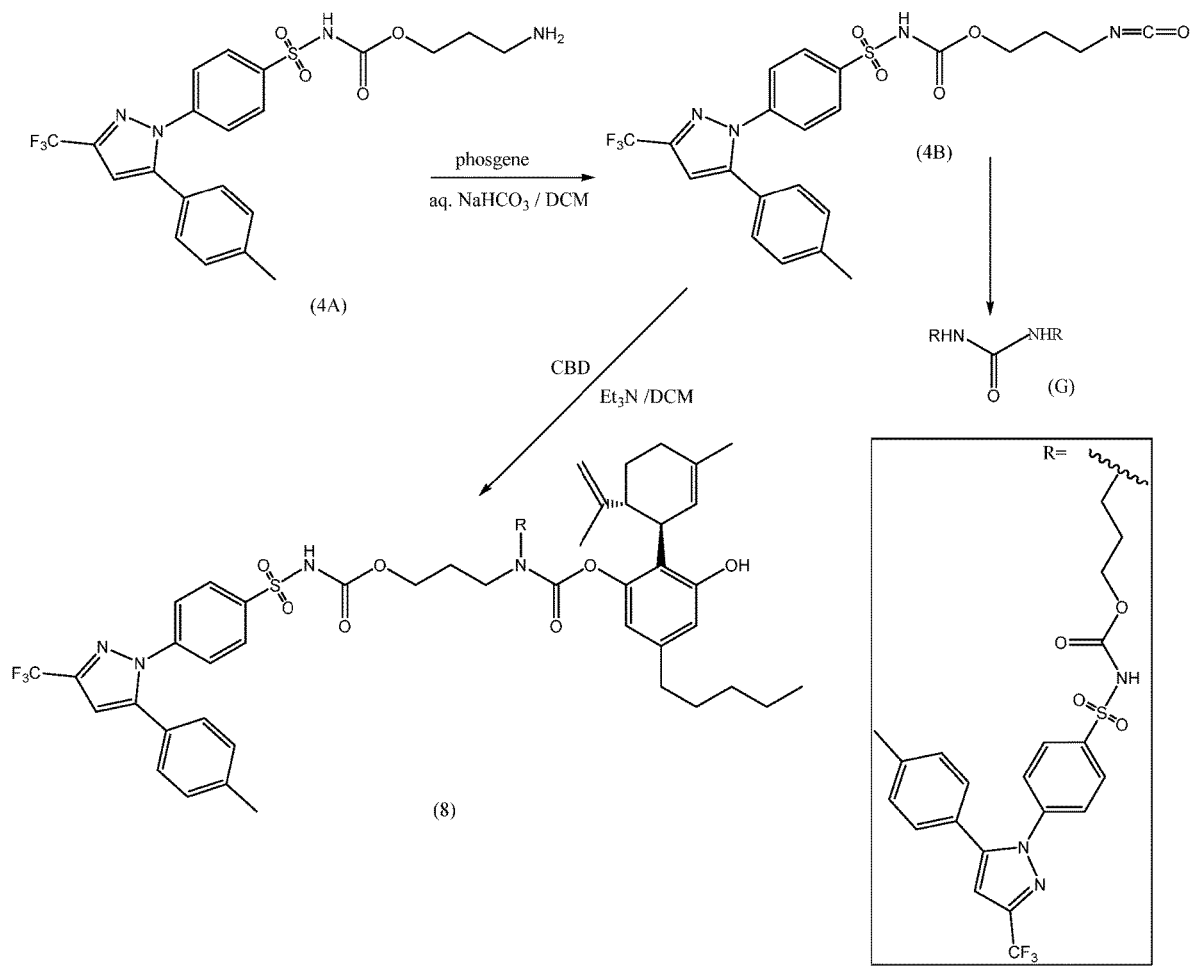
FIG. 3 illustrates a second comparative synthetic route which was not successful in producing the desired conjugate molecule.

Another alternative synthesis reaction was attempted for conjugate molecule (8), as illustrated in FIG. 3. As designed, the primary intermediate molecule (4A) was converted into an isocyanate (4B) using a phosgene solution and an aqueous NaHCO₃ DCM solution, although there was some possibility of forming a urea byproduct (G). The isocyanate could then be reacted directly with protected or unprotected CBD in triethylamine and DCM to obtain the conjugate molecule (8).

LCMS indicated that some product having the expected mass was produced, but the yield was very low, and there were large peaks of unreacted CBD and the urea byproduct. Changing the order of addition and the amounts of each reactant was done, but this did not improve the yield.

Comparative Example 3

The synthesis of molecule (H), illustrated below, was tried:

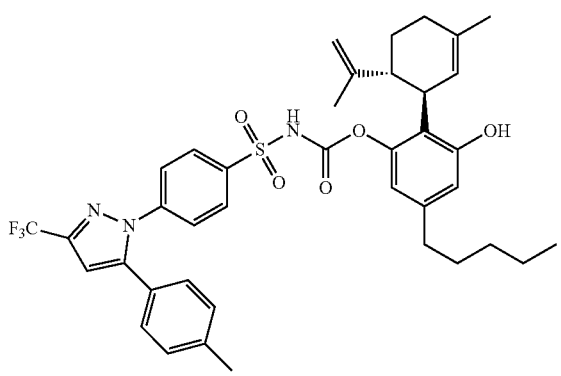

(H)

Multiple different reactions were tried, including those described in FIGS. 1A-1B, FIGS. 2A-2B, and FIG. 3. Different reagent ratios, temperatures, bases, and addition sequences were tried. However, no product with the expected mass was ever isolated and confirmed to be molecule (H) by any analytical test.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A conjugate molecule of either of the following structures:

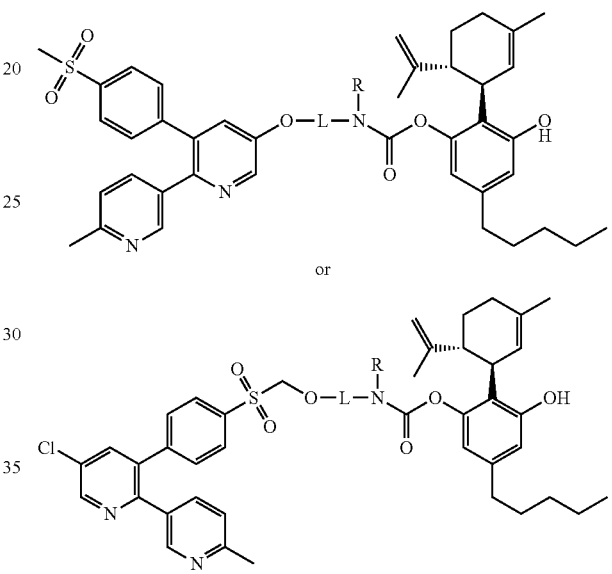

or wherein L is alkyl; and
wherein R is hydrogen or alkyl.

2. The conjugate molecule of claim 1, wherein L contains 3 to 5 carbon atoms.

3. The conjugate molecule of claim 1, wherein R is hydrogen or contains 1 to 3 carbon atoms.

4. A composition comprising the conjugate molecule of claim 1.

* * * * *